US012527676B2

(12) United States Patent
Lee

(10) Patent No.: US 12,527,676 B2
(45) Date of Patent: Jan. 20, 2026

(54) JOINT FIXATION DEVICE AND STEPLESS ANGLE ADJUSTMENT DEVICE THEREOF

(71) Applicant: E-LIFE INTERNATIONAL CO., LTD., New Taipei (TW)

(72) Inventor: Shih-Hsiang Lee, New Taipei (TW)

(73) Assignee: E-Life International Co., Ltd, New Taipei (CN)

( * ) Notice: Subject to any disclaimer, the term of this patent is extended or adjusted under 35 U.S.C. 154(b) by 152 days.

(21) Appl. No.: 18/432,656

(22) Filed: Feb. 5, 2024

(65) Prior Publication Data

US 2025/0248836 A1 Aug. 7, 2025

(51) Int. Cl.
*A61F 5/01* (2006.01)

(52) U.S. Cl.
CPC .... *A61F 5/0102* (2013.01); *A61F 2005/0167* (2013.01)

(58) Field of Classification Search
CPC ............ A61F 5/0102; A61F 2005/0158; A61F 2005/0165; A61F 2005/0167; A61F 2005/0179; A61F 2005/0197; A47C 1/03238; E05D 3/00; E05D 3/02; E05D 3/04; E05D 5/10; E05D 5/12; E05D 5/14; E05D 5/16; E05D 7/00; E05D 7/04; E05D 7/06; E05D 7/10; E05D 11/06; E05D 11/10; E05D 11/1007; E05D 11/1014; E05D 11/1028; E05D 11/1078; B21D 53/40; Y10T 403/32861; Y10T 403/32868; Y10T 403/32877; Y10T 403/32885; Y10T 403/32893; Y10T 403/32901; Y10T 403/32909; Y10T 403/32951; Y10T 403/32967
USPC ............... 602/16; 16/326–332; 292/347–357
See application file for complete search history.

(56) References Cited

U.S. PATENT DOCUMENTS 5,860,943 A * 1/1999 Bloedau ................ A61F 5/0193 16/354
2009/0275944 A1* 11/2009 Huebner ................ A61B 17/60 606/54
2017/0298981 A1* 10/2017 Ásgeirsson ............. F16C 11/10
2024/0254819 A1* 8/2024 Bruchu ................. E05F 1/1008
2024/0358537 A1* 10/2024 Davis .................... A61F 5/0127

* cited by examiner

*Primary Examiner* — Rachael E Bredefeld
*Assistant Examiner* — Seth R. Brown
(74) *Attorney, Agent, or Firm* — Snell & Wilmer L.L.P.

(57) ABSTRACT

A joint fixation has a stepless angle adjustment device having a first body, a second body, a pivot shaft, and a knob assembly. The first body has a first fixing portion. The second body has a second fixing portion. The pivot shaft has a first end fixed to the first body and a second end opposite to the first end and extending into the second body. The first body is rotatable relative to the second body around the pivot shaft. The knob assembly is disposed at the second end of the pivot shaft. When the knob assembly is pulled, the knob assembly is capable of driving the first body to rotate relative to the second body around the pivot shaft. Angle adjustment between the first body and the second body is easy and may be done by one hand.

9 Claims, 7 Drawing Sheets

JOINT FIXATION DEVICE AND STEPLESS ANGLE ADJUSTMENT DEVICE THEREOF

BACKGROUND OF THE INVENTION

1. Field of the Invention

The present invention relates to a medical equipment, especially to a body brace or an assistive device.

2. Description of the Prior Arts

When people are injured or aging, support strength provided by muscles is insufficient to keep a joint at a proper angle. Therefore, the angle of the joint has to be maintained by a joint fixator to keep a human body in correct posture for daily life or to prevent further injuries. As the human body recovers, a movable angle of the joint gradually changes, and hence the joint fixator needs to be adjusted gradually according to the condition of the human body. However, a conventional joint fixator is not easily operated, and a tool may be further required for adjustment. That is very inconvenient.

To overcome the shortcomings, the present invention provides a joint fixation device and a stepless angle adjustment device thereof to mitigate or obviate the aforementioned problems.

SUMMARY OF THE INVENTION

The main objective of the present invention is to provide a joint fixation device and a stepless angle adjustment device thereof that can be easily adjusted in angle to fit a user' body condition.

The joint fixation device comprises a stepless angle adjustment device. The stepless angle adjustment device comprises a first body, a second body, a pivot shaft, and a knob assembly. The pivot shaft has a first end fixed to the first body and a second end extending into the second body. The first body is rotatable relative to the second body around the pivot shaft. The knob assembly is disposed at the second end of the pivot shaft and is capable of driving the first body to rotate relative to the second body around the pivot shaft.

When the joint fixation device is in use, the knob assembly is firstly pulled, and then is rotated to drive the first body to rotate relative to the second body. Whereby, adjustment of an angle between the first body and the second body is easy, and even can be done by one single hand of the user. After the angle adjustment is done, the first body is connected to a back or a shoulder of a human body, and the second body is connected to a waist of the human body. Accordingly, angle adjustment of the joint fixation device is easy and stepless.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
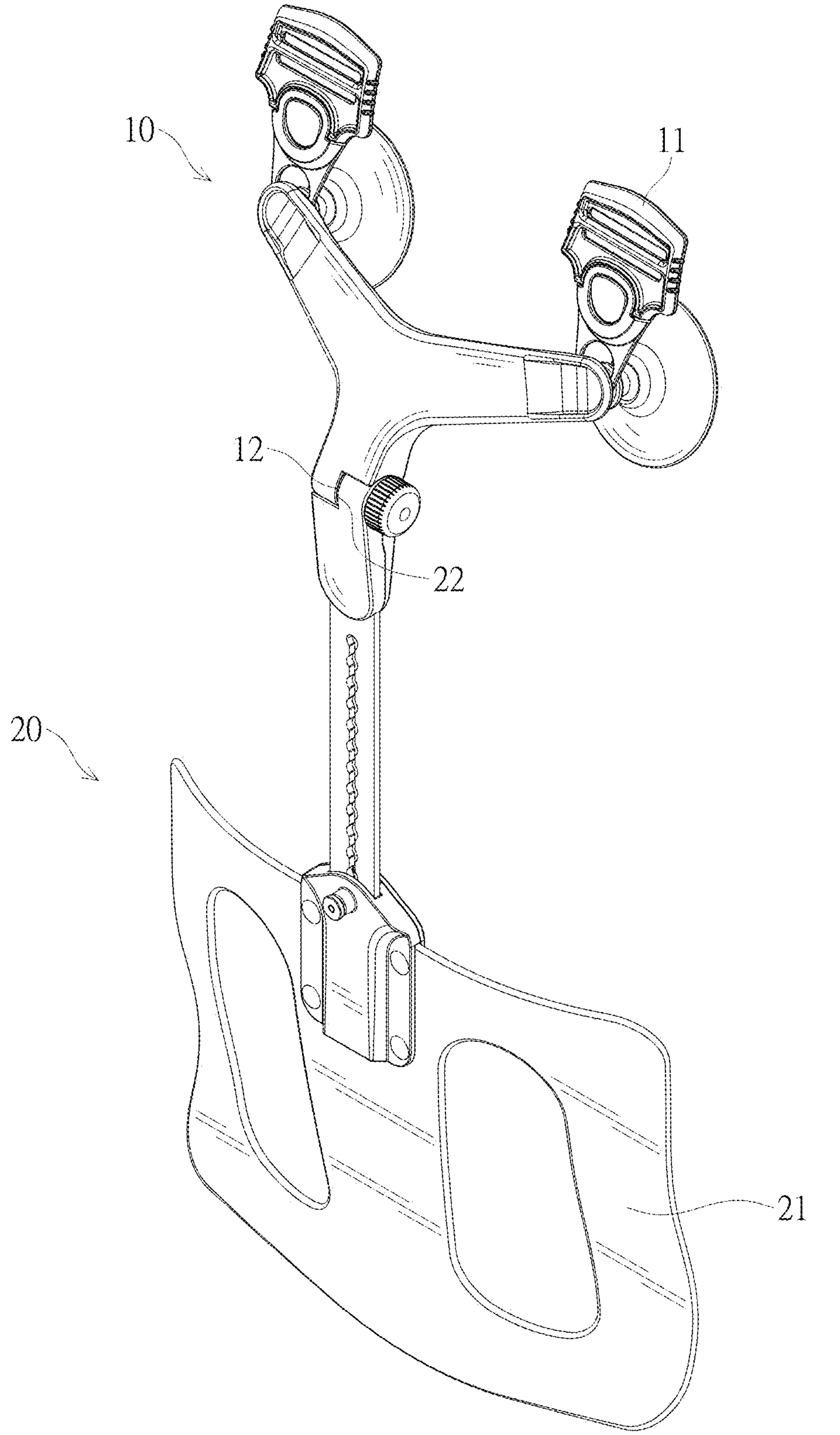
FIG. 1 is a perspective view of a joint fixation device in accordance with the present invention.

With reference to FIG. 1, a joint fixation device in accordance with the present invention is adapted to support joints in a human body to keep the joints at proper angles. For example, as shown in FIG. 1, in the embodiment, the joint fixation device is a spine brace to fix spinal joints of the human body and for supporting a spine of the human body at a suitable angle. The joint fixation device has a stepless angle adjustment device and a fastener, e.g. a hook and loop fastener or a belt, for fixing the stepless angle adjustment device to the human body.

Figure 2:
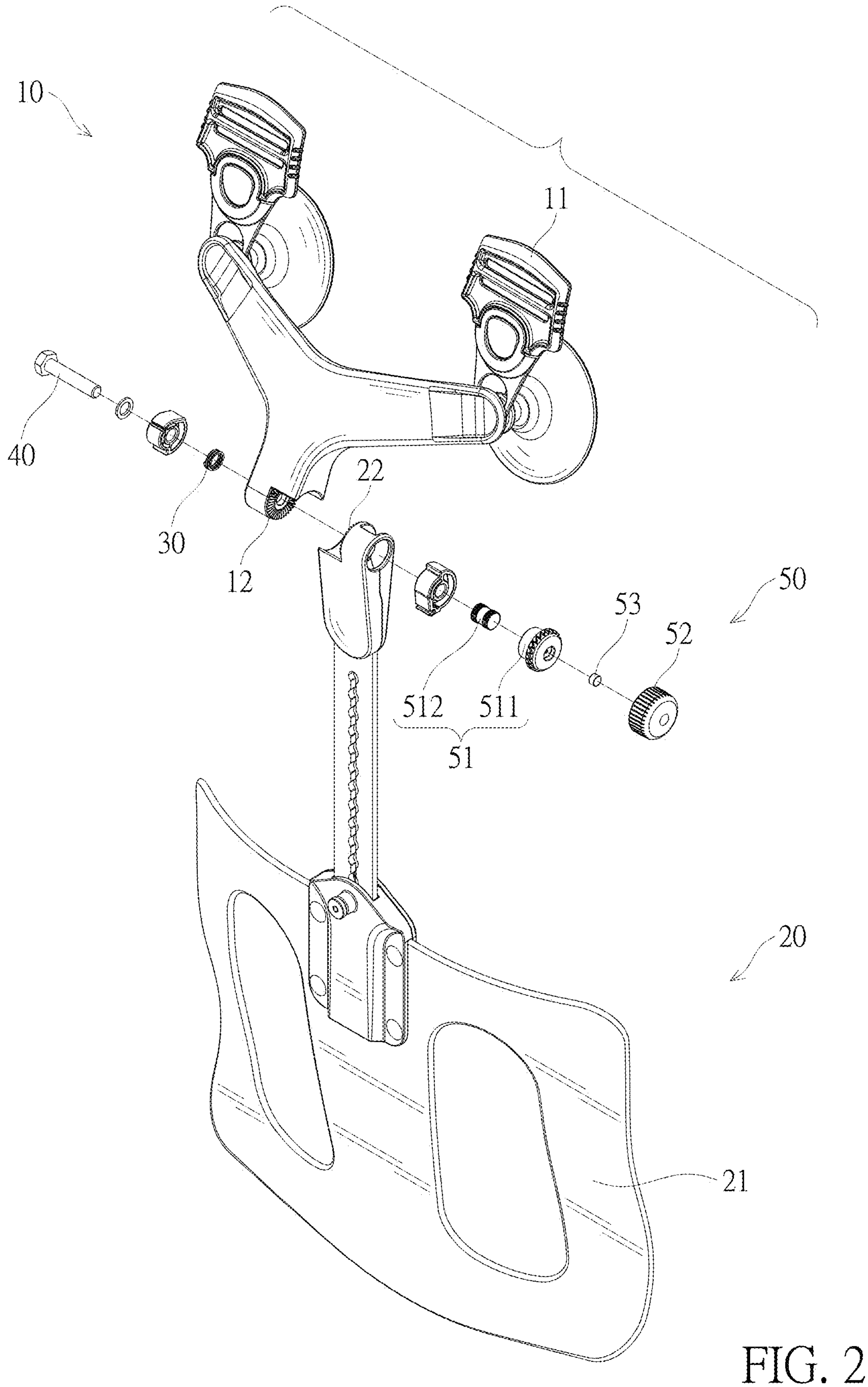
FIG. 2 is an exploded perspective view of the joint fixation device in FIG. 1.
Figure 3:
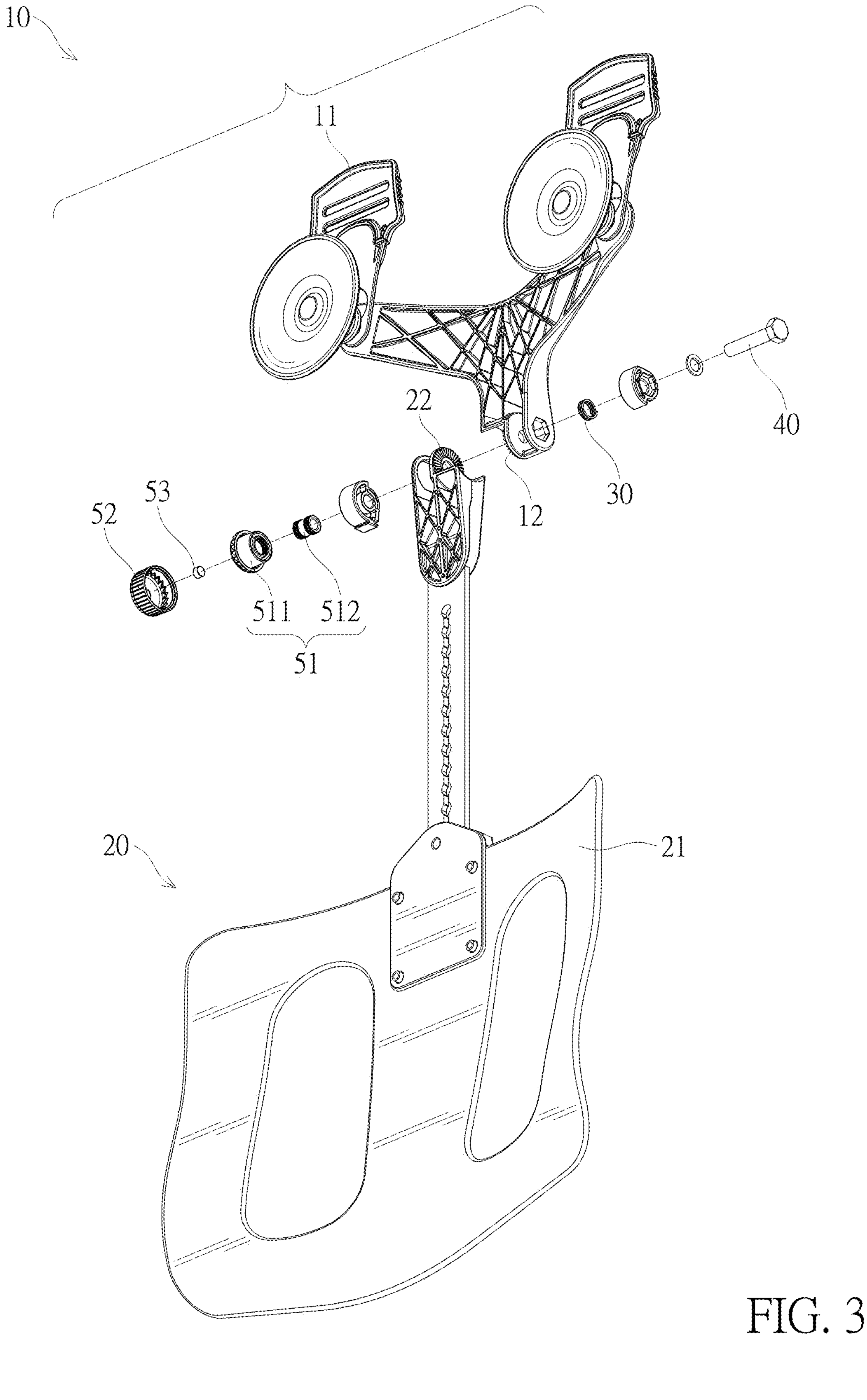
FIG. 3 is another exploded perspective view of the joint fixation device in FIG. 1.
Figure 4:
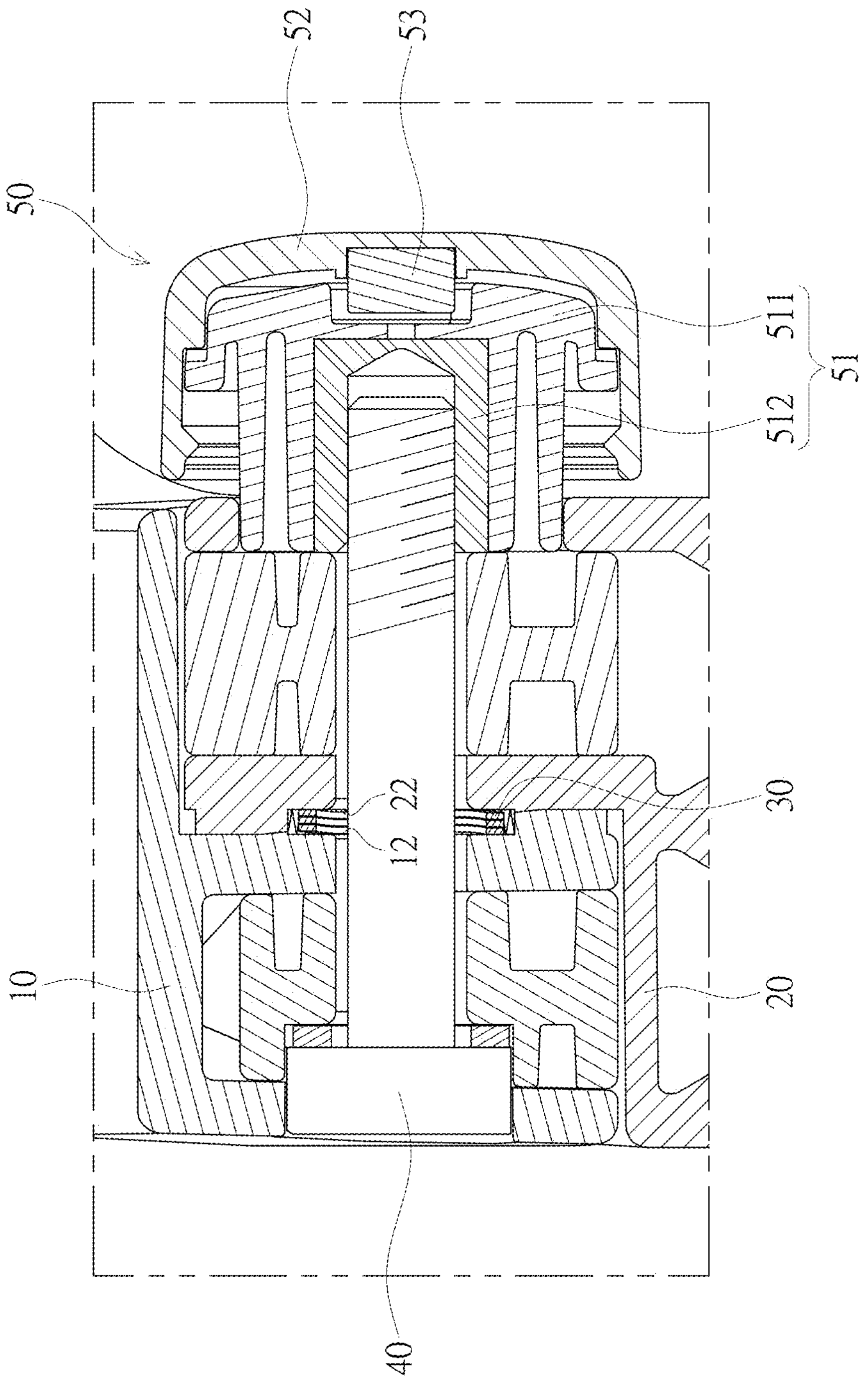
FIG. 4 is an enlarged cross-sectional view of a stepless angle adjustment device of the joint fixation device in FIG. 2.

With reference to FIGS. 2 to 4, the stepless angle adjustment device comprises a first body 10, a second body 20, a resilient member 30, a pivot shaft 40, and a knob assembly 50. The first body 10 includes a first fixing portion 11. The second body 20 includes a second fixing portion 21. In the embodiment, the joint fixation device is adapted to fix the spinal joints, so the first fixing portion 11 is adapted to be fixed at a back of the human body, and the second fixing portion 21 is adapted to be fixed at a waist of the human body. In another embodiment, the first fixing portion 11 may be fixed at the waist and the second fixing portion 21 may be fixed at the back.

Furthermore, in other embodiments, when the joint fixation device is adapted to fix a knee joint, the first fixing portion 11 may be fixed at a thigh of the human body and the second fixing portion 21 may be fixed at a calf of the human body, and vice versa. When the joint fixation device is adapted to fix an elbow joint, the first fixing portion 11 may be fixed at an arm of the human body and the second fixing portion 21 may be fixed at a wrist of the human body. When the joint fixation device is adapted to fix joints in a neck, the first fixing portion 11 may be fixed at a head and the second fixing portion 21 may be fixed at a shoulder. That is, the joint fixation device is applicable for fixing various joints.

In the embodiment, the first body 10 includes a first crown toothed portion 12. The second body 20 includes a second crown toothed portion 22 selectively engaging with the first crown toothed portion 12. When the first crown toothed portion 12 and the second crown toothed portion 22 engage with each other, the first body 10 and the second body 20 are non-rotatable relative to each other. It is not limited to this, as it may be an angular fixing structure for fixing an angle between the first body 10 and the second body 20. The resilient member 30 is disposed between the first body 10 and the second body 20 pressing the first crown toothed portion 12 of the first body 10 and the second crown toothed portion 22 of the second body 20 toward separating from each other, and hence the first body 10 and the second body 20 are rotatable relative to each other.

The pivot shaft 40 has a first end and a second end opposite to each other. The first end is fixed to the first body 10. The second end extends into the second body 20.

Whereby, the pivot shaft 40 and the first body 10 are non-rotatable relative to each other, and the second body 20 is rotatable around the pivot shaft 40. In other words, when the second body 20 rotates around the pivot shaft 40, an angle between the second body 20 and the first body 10 is adjusted.

In the embodiment, the second body 20 is disposed between the knob assembly 50 and the first body 10. Specifically, the knob assembly 50 is disposed to the second end of the pivot shaft 40 and is capable of driving the first body 10 to rotate relative to the second body 20 around the pivot shaft 40.

The knob assembly 50 includes a sleeve set 51, a rotating cap 52, and a magnetic member 53. The sleeve set 51 is fixed to the second end of the pivot shaft 40, so the second body 20 is disposed between the sleeve set 51 and the first body 10. In the embodiment, the sleeve set 51 includes a first sleeve member 511 and a second sleeve member 512. The first sleeve member 511 includes an engaging toothed portion formed around an external peripheral surface thereof. Preferably, the engaging toothed portion is ratchet teeth. The first sleeve member 511 is slidably sleeved on and surrounds the second sleeve member 512. The first sleeve member 511 has an internal toothed portion formed around an internal peripheral surface thereof. The second sleeve member 512 has an external toothed portion formed around an external peripheral surface thereof. The first sleeve member 511 and the second sleeve member 512 engage with each other via an engagement of the internal toothed portion of the first sleeve member 511 and the external toothed portion of the second sleeve member 512. The first sleeve member 511 and the second sleeve member 512 are non-rotatable relative to each other but are slidable relative to each other along an axial direction of the sleeve set 51. The second sleeve member 512 is fixed to the second end of the pivot shaft 40. Accordingly, when the first sleeve member 511 is rotated, the second sleeve member 512 and the pivot shaft 40 are rotated with the first sleeve member 511.

The rotating cap 52 is disposed to the sleeve set 51. Specifically, the rotating cap 52 is fixed to the first sleeve member 511, so the rotating cap 52 is capable of driving the first sleeve member 511, the second sleeve member 512, and the pivot shaft 40 to rotate. The rotating cap 52 selectively engages with the engaging toothed portion of the first sleeve member 511 of the sleeve set 51. When the rotating cap 52 engages with said engaging toothed portion, the sleeve set 51 is driven to unidirectionally rotate by the rotating cap 52, and the pivot shaft 40 and the first body 10 are rotated with the sleeve set 51 to adjust the angle between the first body 10 and the second body 20.

The magnetic member 53 is fixed to the rotating cap 52. The magnetic member 53 and the pivot shaft 40 magnetically attract each other. Accordingly, the pivot shaft 40 drives the first crown toothed portion 12 of the first body 10 toward engaging with the second crown toothed portion 22 of the second body 20. In another embodiment, the magnetic member 53 may be omitted, and the rotating cap 52 is magnetic and can be magnetically attracted to the pivot shaft 40.

Figure 5:
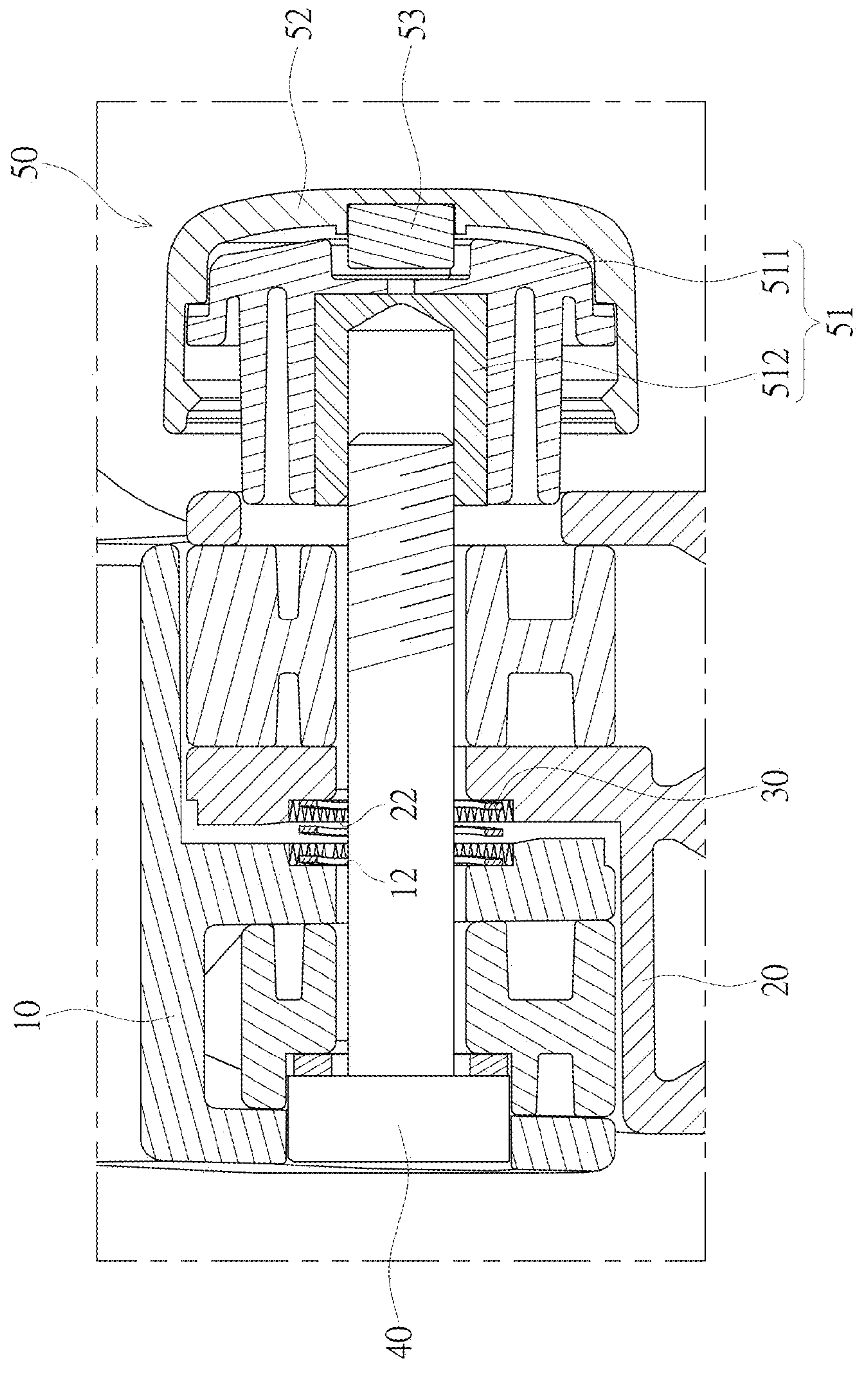
FIG. 5 is an operational enlarged cross-sectional view of a stepless angle adjustment device of the joint fixation device showing that a knob assembly is pulled.
Figure 6:
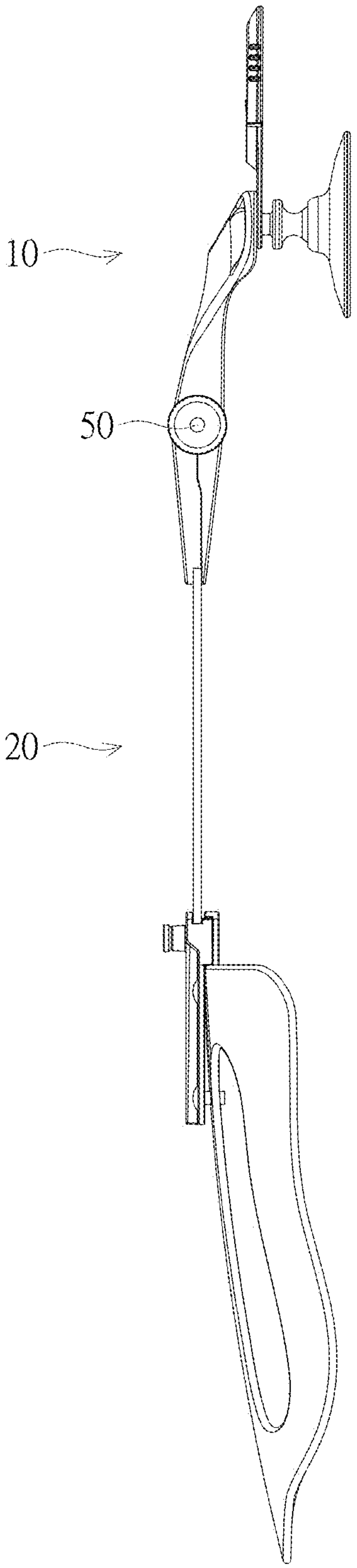
FIG. 6 is a side view of the joint fixation device in FIG. 1.
Figure 7:
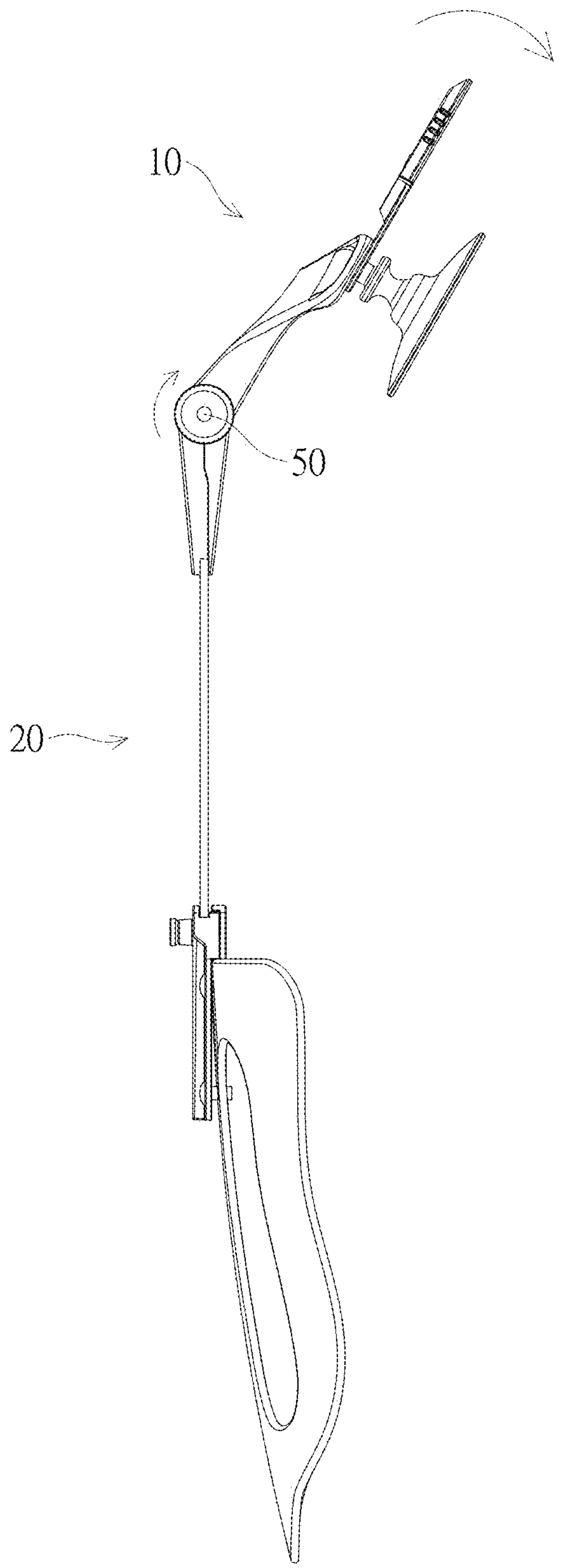
FIG. 7 is an operational side view of the joint fixation device in FIG. 1 showing that an angle between the first body and the second body is adjusted.

With reference to FIGS. 4 to 6, with the foregoing structures, when the joint fixation device is in use, the rotating cap 52 is pulled to increase a distance between the magnetic member 53 and the pivot shaft 40, whereby magnetic attraction between the magnetic member 53 and the pivot shaft 40 is reduced and cannot counteract the resilience of the resilient member 30. Accordingly, the first body 10 and the second body 20 are pushed away from each other by the resilient member 30, and the first crown toothed portion 12 and the second crown toothed portion 22 disengage from each other. The first body 10 and the second body 20 are rotatable relative to each other accordingly. Next, the rotating cap 52 is rotated to drive the first sleeve member 511 and the second sleeve member 512 of the sleeve set 51, the pivot shaft 40, and the first body 10 to rotate. The angle between the first body 10 and the second body 20 is adjusted.

Afterwards, the first body 10 is connected to the back of the human body or further connected to the shoulder of the human body, and the second body 20 is connected to the waist of the human body. Angle adjustment between the first body 10 and the second body 20 is easily achieved and can be done by one single hand. Accordingly, angle adjustment of the joint fixation device is easy and stepless.

What is claimed is:

1. A stepless angle adjustment device comprising:
- a first body;
- a second body;
- a pivot shaft having:
  - a first end fixed to the first body; and
  - a second end extending into the second body for the first body to rotate relative to the second body around the pivot shaft; and
- a knob assembly disposed at the second end of the pivot shaft and being capable of driving the first body to rotate relative to the second body around the pivot shaft, and the knob assembly including:
  - a sleeve set having:
    - a first sleeve member having an engaging toothed portion formed around an external peripheral surface of the first sleeve member; and
    - a second sleeve member fixed to the second end of the pivot shaft, and the first sleeve member slidably sleeved on and surrounding the second sleeve member; and
  - a rotating cap selectively engaging with the engaging toothed portion of the first sleeve member;
- when the rotating cap engages with the engaging toothed portion of the first sleeve member of the sleeve set, the rotating cap is capable of driving the sleeve set to rotate, and the pivot shaft and the first body are rotated with the sleeve set.

2. The stepless angle adjustment device as claimed in claim 1, wherein
- the first body includes a first crown toothed portion; and
- the second body includes a second crown toothed portion selectively engaging with the first crown toothed portion;
- the knob assembly includes a magnetic member fixed to the rotating cap;
- the magnetic member magnetically attracts the pivot shaft, such that the pivot shaft drives the first crown toothed portion of the first body toward engaging with the second crown toothed portion;
- the stepless angle adjustment device comprises a resilient member disposed between the first body and the second body, such that the first crown toothed portion is pressed toward separating from the second crown toothed portion.

3. The stepless angle adjustment device as claimed in claim 1, wherein the engaging toothed portion of the first sleeve member of the sleeve set is ratchet teeth.

4. A joint fixation device comprising:
- a stepless angle adjustment device comprising:
  - a first body including a first fixing portion;
  - a second body including a second fixing portion;

a pivot shaft having:

a first end fixed to the first body; and a second end extending into the second body for the first body to rotate relative to the second body around the pivot shaft; and a knob assembly disposed at the second end of the pivot shaft and being capable of driving the first body to rotate relative to the second body around the pivot shaft, and the knob assembly including:

a sleeve set having a first sleeve member having an engaging toothed portion formed around an external peripheral surface of the first sleeve member; and a second sleeve member fixed to the second end of the pivot shaft, and the first sleeve member slidably sleeved on and surrounding the second sleeve member; and a rotating cap selectively engaging with the engaging toothed portion of the first sleeve member;

when the rotating cap engages with the engaging toothed portion of the first sleeve member of the sleeve set, the rotating cap is capable of driving the sleeve set to rotate, and the pivot shaft and the first body are rotated with the sleeve set.

5. The joint fixation device as claimed in claim 4, wherein the first body includes a first crown toothed portion; and the second body includes a second crown toothed portion selectively engaging with the first crown toothed portion;

the knob assembly includes a magnetic member fixed to the rotating cap;

the magnetic member magnetically attracts the pivot shaft, such that the pivot shaft drives the first crown toothed portion of the first body toward engaging with the second crown toothed portion;

the stepless angle adjustment device comprises a resilient member disposed between the first body and the second body, such that the first crown toothed portion is pressed toward separating from the second crown toothed portion.

6. The joint fixation device as claimed in claim 4, wherein the engaging toothed portion of the first sleeve member of the sleeve set is ratchet teeth.

7. The joint fixation device as claimed in claim 4, wherein the first fixing portion is adapted to fix at a back of a human body, and the second fixing portion is adapted to fix at a waist of the human body.

8. The joint fixation device as claimed in claim 5, wherein the first fixing portion is adapted to fix at a back of a human body, and the second fixing portion is adapted to fix at a waist of the human body.

9. The joint fixation device as claimed in claim 4, wherein the first fixing portion is adapted to fix at a back of a human body, and the second fixing portion is adapted to fix at a waist of the human body.

* * * * *